Figure 1:
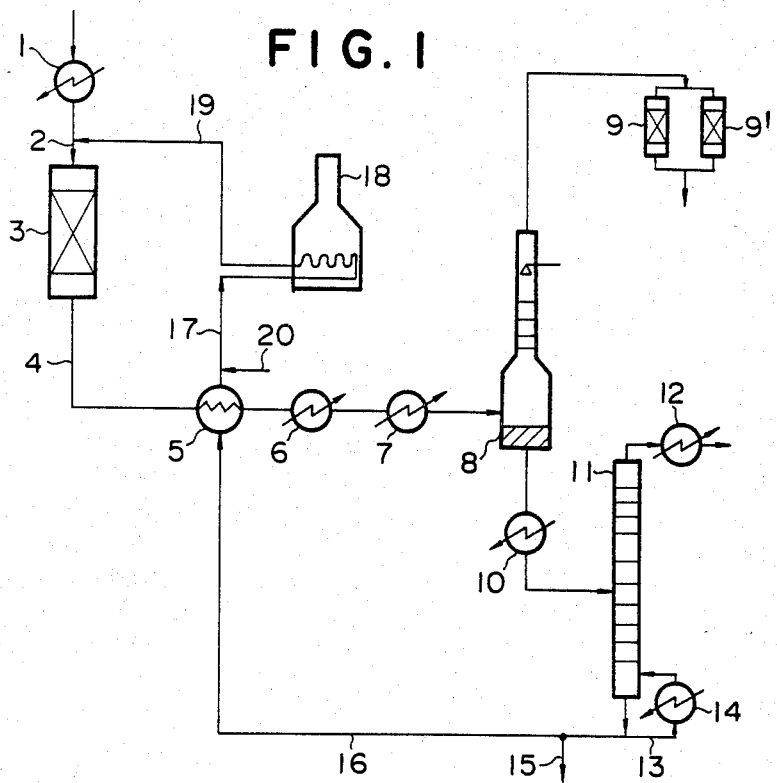

United States Patent [19]

Kida et al.

[11] Patent Number: 4,536,605

[45] Date of Patent: Aug. 20, 1985

[54] PROCESS FOR THE PRODUCTION OF TERTIARY OLEFIN

[75] Inventors: Koichi Kida, Toyosaka; Yoshio Kawai, Niigata; Yutaka Tamura, Niigata; Yoshiharu Suzuki, Niigata, all of Japan

[73] Assignee: Mitsubishi Gas Chemical Co., Inc., Tokyo, Japan

[21] Appl. No.: 371,424

[22] Filed: Apr. 23, 1982

Related U.S. Application Data

[63] Continuation-in-part of Ser. No. 280,071, Jul. 2, 1981, Pat. No. 4,343,959.

[30] Foreign Application Priority Data

Jul. 25, 1980 [JP] Japan .................................. 55-102074
Jan. 14, 1982 [JP] Japan ..................................... 57-4325

[51] Int. Cl.³ ................................................ C07C 1/00
[52] U.S. Cl. .................................... 585/640; 585/733
[58] Field of Search ........................................ 585/640

[56] References Cited

U.S. PATENT DOCUMENTS 4,260,841 4/1981 Holland et al. ...................... 585/640
4,278,565 7/1981 Chen et al. ........................... 585/640
4,296,266 10/1981 Wunder et al. ...................... 585/640
4,343,959 8/1982 Kida et al. ............................ 585/640

Primary Examiner—Curtis R. Davis
Attorney, Agent, or Firm—Douglas W. Wyatt; Eliot S. Gerber; Guy W. Shoup

[57] ABSTRACT

A tertiary olefin is produced by contacting a gaseous tertiary ether usually represented by the following general formula:

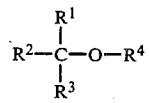

wherein $R^1$, $R^2$ and $R^3$ are alkyl groups each having 1-4 carbon atoms which may be same or different and $R^4$ is an alkyl group having 1-3 carbon atoms, with a catalyst obtained by calcining a silica-alumina compound at 700°–1100° C. in order to effect cracking of the tertiary ether. This reaction may be carried out in the presence of steam to result in further improvements.

14 Claims, 2 Drawing Figures

PROCESS FOR THE PRODUCTION OF TERTIARY OLEFIN

This is a continuation-in-part of U.S. application Ser. No. 280,071, filed July 2, 1981, now U.S. Pat. No. 4,343,959.

The present invention relates to a process for the production of the corresponding tertiary olefin from a tertiary ether (sometimes referred to "TE" hereinafter). More particularly, it relates to a process for the production of the corresponding tertiary olefin from a tertiary ether in high purity and at high yield using a novel catalyst.

In recent years, the production of large volumes of methyl-tert-butyl ether (hereinafer referred to as MTBE) has been carried out in Japan, Europe and the U.S.A. for use as an octane booster for gasoline. It is expected that in the future the production of isobutylene obtained by the cracking of MTBE will be overwhelmingly advantageous compared to conventional sulfuric acid extraction processes using the C4 fraction. As one of prior conditions, it is necessary that the cracking reaction of MTBE proceeds at high conversion (high cracking ratio) and high selectivity. It is also desirable that isobutylene and methanol which are produced by cracking be of high purity for use as industrial raw materials.

A tertiary olefin having a high purity is a useful material in industries; for instance, isobutylene having a high purity is expected to be used as the raw material for the production of butylene rubber, MMA and the like.

The cracking of MTBE can be conducted in the liquid phase at a temperature not higher than 150° C. in the presence of an acid in accordance with the following equilibrium reaction:

$$\text{MTBE} \underset{}{\overset{H^+}{\rightleftharpoons}} \text{i-C}_4\text{H}_8 + \text{CH}_3\text{OH}.$$

However, for best results it is appropriate to carry out the catalytic reaction in the vapor phase at a temperature not lower than 180° C. There is found a description in, for instance, "Chemical abstracts" 59. 11231f (1963), that this reaction is carried out on the surface of activated alumina at a temperature of 175°–380° C. under normal pressure. Also, in U.S. Pat. No. 3,170,000 it is described that satisfactory results were obtained by the use of a solid catalyst such as alumina or magnesia having a low specific surface area. However, in this case, the reaction should be carried out at high temperatures because of the low activity of the catalyst. None the less, the conversion is not higher than 70% resulting in the necessity to recover unreacted MTBE. Though this MTBE can usually be recovered by distillation, mixtures of methanol with MTBE can not be avoided. The results in the production of dimethyl ether and difficulty in separating it from isobutylene. In order to minimize the amount of unreacted MTBE, it is necessary to increase the one-pass conversion. For this purpose, the temperature is further increased and the catalyst contact time is extended. Still dimethyl ether is easily produced as a by-product. Consequently, the production of by-product dimethyl ether can not be avoided in both cases.

Japanese Patent Publication No. 41882/1972 discloses a process in which cracking of MTBE is carried out using an acidic solid catalyst having a specific surface area of 25 m²/g or more, as exemplified by γ-alumina. According to this process, conversion of MTBE as well as selectivity of isobutylene and selectivity of methanol are unsatisfactorily low in practical application, and also formation of the by-product dimethylether cannot be avoided.

DEOS No. 2534544 discloses cracking of a tertiary ether in the presence of a catalyst of an activated alumina which is modified by the reaction with an organosilicon compound. However, in this process, although the selectivity was improved by carrying out the cracking of MTBE at a low temperature and thereby reducing the conversion of MTBE, the production of by-product dimethyl ether was increased when the conversion was increased. Consequently it was impossible to increase both conversion and selectivity. Also, organosilicon catalysts are expensive.

In DEOS No. 2924869, there is described a cracking reaction which proceeds almost quantitatively using a catalyst comprising silica as the main component together with various metal oxides, particularly 0.2% of alumina. However, silica itself has no catalytic activity when it is used alone. When alumina was combined with silica, the cracking of MTBE was, according to tests conducted by the present inventors, satisfactory. However, also the polymerization activity of isobutylene increased and the cracking activity decreased quickly so that no satisfactory result was obtained. Even though it is assumed that a catalyst of the process having a very low concentration of alumina shows suitable activity for cracking in the narrow range of from no activity to high activity, it is difficult to obtain a catalyst which gives a satisfactory result with high reproducibility. The industrial use of such a catalyst is considered to be impossible.

In Derwent (CPI) 15070W/09 j49094-602, a process for the cracking of MTBE giving excellent results is described using an activated carbon catalyst. However, according to tests conducted by the present inventors, when the activated carbon catalyst is used, additional carbon which seems to be produced from the olefins in reaction products deposits. As a result, the operation of reactivation of the activated carbon catalyst to remove the carbon deposited by reaction with oxygen can not be conducted because the catalyst activated carbon burns out together with the carbon deposited. Thus, it was found that the catalyst must be frequently replaced with a new charge.

As mentioned above, in a case wherein conventional processes are used, even though the conversion of tertiary ether or the selectivities of tertiary olefin and primary alcohol are satisfactory, there are defects such as the difficulty of increasing both conversion and selectivity, low reproducibility depending upon catalyst, high cost of catalyst, complexity of catalyst preparation, short life of catalyst and difficulty of regenerating catalyst. Consequently, these processes are not suitable for practical uses.

The process of the present invention avoids the defects of conventional processes and provides a catalyst which has the advantages of high cracking activity, selectivity, and reporducibility as well as low cost, long life and high stability.

It has been found that a catalyst which is useful for the practice of this invention can be provided by calcining ordinary silica-alumina under specific conditions.

The present invention provides a process to produce a tertiary olefin which comprises contacting a gaseous tertiary ether with a catalyst obtained by calcining a silica-alumina compound at 700°–1100° C.

It has also been found that by the use of steam in the reaction system, the conversion of the tertiary ether as well as the selectivity of the tertiary olefin and the primary alcohol can be further improved while elongating catalyst life.

The present invention, therefore includes a process for producing a tertiary olefin from a corresponding tertiary ether which comprises contacting a gaseous tertiary ether in the presence of steam with a catalyst obtained by calcining a silica-alumina compound at 700°–1100° C.

Figure 2:
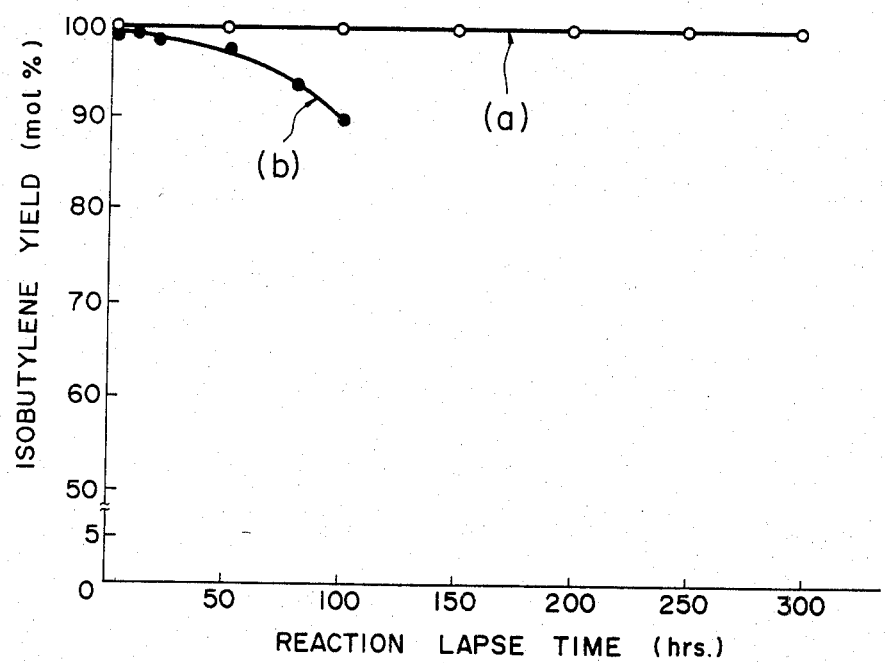

In the accompanying drawings:

FIG. 1 is a flow sheet for practicing one embodiment of the present invention where the reaction is carried out in the presence of steam; and FIG. 2 is a graph indicating the catalyst activity with lapse of time, the straight line (a) showing the case when steam is permitted to be present in the reaction system and the curve (b) showing the case when there is no steam in the reaction system.

Silica-alumina compounds used in the present invention include, for example, natural silica-alumina compounds such as acidic clay and activated clay which contain silica-alumina and other impurities, as well as synthetic silica-alumina compounds obtained, for instance, by depositing an aluminum component on the surface of a silica hydrogel and the like. Silica-alumina compounds on the market as catalysts for other reactions may also be employed. A third component other than silica-alumina may be present; however, both silica and alumina must be present. In general, the silica-alumina compound will contain 2–98 wt.% silica and 98–2 wt% alumina based on the total weight of silica and alumina.

These silica-alumina compounds are calcined at 700°–1100° C., preferably 750°–1000° C. When the calcination temperature is lower than 700° C., side-reactions such as polymerization or dehydration can not be suppressed. When the calcination temperature exceeds 1100° C., the cracking activity is remarkably lowered. Satisfactory conversion of TE cannot be obtained at either higher reaction temperatures or lower reaction temperatures.

The calcination time may be 0.5–50 hours, preferably 2–24 hours. It will be appropriately selected in accordance with the calcination temperature and catalyst composition. When a silica-alumina compound has a high silica content, it is preferable to somewhat lower the calcination temperature or shorten the calcination time. When the alumina content is high, the calcination time gives little effect in the disclosed range of calcination temperature. Although the calcination may be conducted in an atmosphere which contains an inert gas such as air, nitrogen, steam or a mixture of them, it is most practical to conduct calcination in air.

There is no limitation to the calcination apparatus. Any conventional apparatus can be used. These include stationary types, for example, a muffle furnace, a gas-passing form one wherein, for example, quartz tubes are used in a cylindrical electric furnace and the like.

It is desirable that calcination be carried out at a constant temperature to promote uniformity of product.

While the catalyst of the present invention has a long life, it has been observed that the activity gradually decreases owing to deposition of small amounts of polymer during use. In such a case the activity can be easily recovered by blowing hot air at a temperature not lower than 500° C. and burning the deposited material. This operation for regeneration may be carried out for a long time or repeated several times, with no deterioration in mechanical strength of the catalyst.

Tertiary ethers suitable for use in the present invention are conventional. They may be represented by the following general formula:

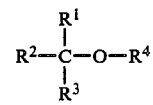

wherein $R^1$, $R^2$ and $R^3$ are alkyl groups each having 1–4 carbon atoms which may be the the same or different from each other. The preferred are alkyl groups having 1–3 carbon atoms, for example, methyl, ethyl and isopropyl groups. $R^4$ is an alkyl group having 1–3 carbon atoms, preferably methyl group or ethyl group. The methyl group is especially preferred.

Typical examples of tertiary ethers represented by this general formula and tertiary olefins obtained therefrom are shown below:

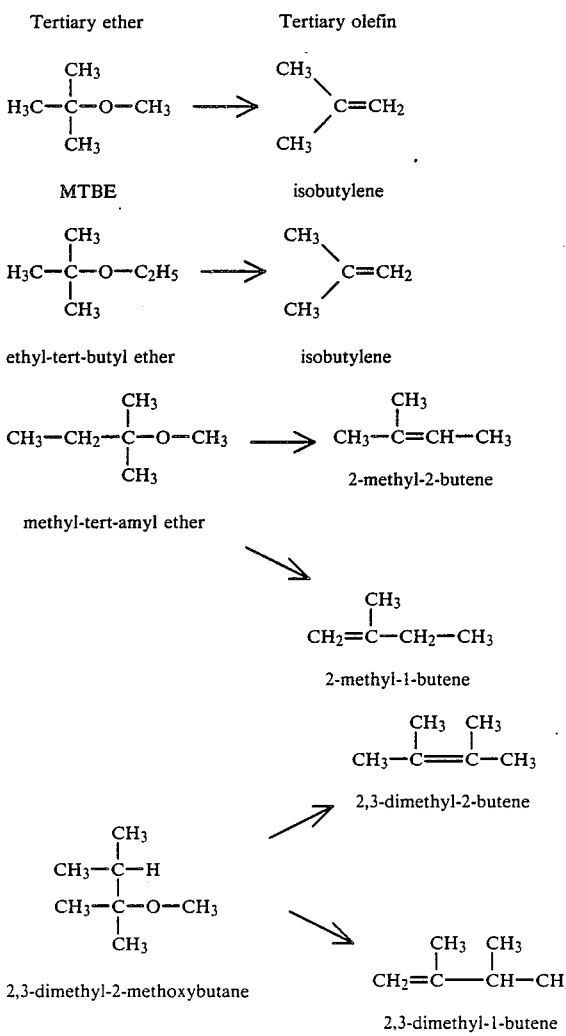

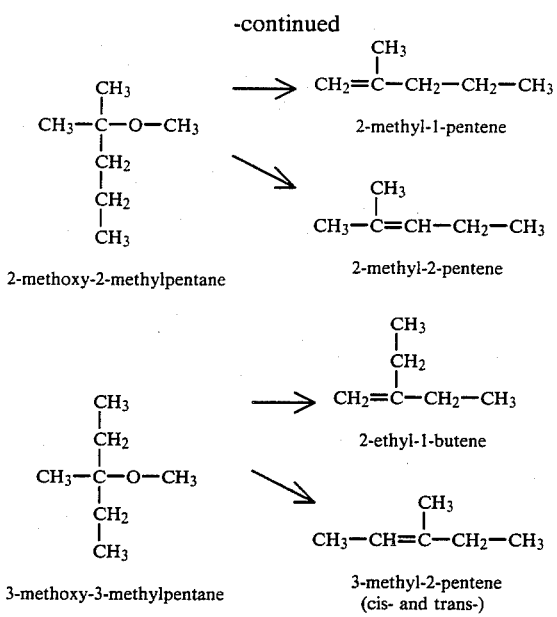

Among them, MTBE, methyl-tert-amyl ether and ethyl-tert-butyl ether are the most desirable for industrial raw material.

These tertiary ethers may be obtained by any of several known methods. For instance, in the case of MTBE, one obtained from isobutylene having a high purity and methanol having a high purity can be used. However, it is preferable to react the industrial $C_4$ fraction containing isobutylene with methanol. This corresponds to extraction of isobutylene from $C_4$ fraction containing isobutylene.

The temperature of cracking reaction when carried out in the absence of steam is 120°–350° C., preferably 170°–300° C. The reaction pressure may be any level at which the tertiary ether is in the gaseous state under the temperature condition. Usually it is desirable to carry out the operation at 0–10 kg/cm² (gauge).

The tendency is for the reaction pressure to lower as the conversion of TE is increased. A sufficiently high conversion can be attained even under a pressure of 5–6 kg/cm² (gauge), and this pressure is suitable for the fractional distillation of tertiary olefin produced. The velocity at which tertiary ether is supplied per unit volume of catalyst (WHSV, g/cc/hr) is 0.3–100 g/cc/hr, preferably 0.5–10 g/cc/hr.

The temperature of cracking reaction in the presence of steam is 150°–400° C., preferably 180°–350° C. The reaction pressure may be any level at which the tertiary ether is in gaseous state under the temperature condition. Usually it is desirable to carry out the operation at 0–20 kg/cm² (gauge), preferably 4–8 kg/cm² (gauge).

The molar ratio of steam to a tertiary ether ($H_2O$/tertiary ether) in the reaction system may be from 0.3–50, preferably 0.5–30.

The reaction according to the present invention may be carried out either batchwise or continuously.

When the reaction is conducted by a continuous process, there is generally employed a fixed-bed system reactor. The type of the fixed-bed system reactor is not particularly limited, but usually there may be employed an adiabatic type, a heat exchange type with feed gas and a multi-tubular system external heating type, etc. Among them, the heat exchange type with feed gas is preferred.

The contact time depends on the reaction temperature, the catalyst employed and other factors. For example, in case of a continuous process, the velocity at which the tertiary ether is supplied per catalyst volume (WHSV g/cc/hr) is 0.3–100 g/cc/hr, preferably 0.5–30 g/cc/hr.

FIG. 1 is a schematic illustration of a process flow sheet for obtaining a tertiary olefin from a tertiary ether by using a fixed-bed system reactor.

In the process, a gaseous tertiary ether pre-heated in a pre-heater 1 is mixed with superheated steam from line 19 and fed into a fixed-bed reactor 3 through line 2. The fixed-bed system reactor 3 is previously filled with an activated catalyst. The tertiary ether is cracked, and the reaction product liquor containing a tertiary olefin and a primary alcohol is discharged from the fixed-bed system reactor 3. The reaction product liquor is delivered through line 4 to a heat exchanger 5, further cooled successively through a cooler 6 and a cooler 7 and then delivered to a decanter 8. In the decanter 8, the reaction product liquor is separated into two layers, an organic layer composed principally of the tertiary olefin and an aqueous layer containing the primary alcohol. The organic layer, while it is ascending through the decanter 8, is washed with water at the upper part of the decanter 8 and thereafter discharged from the top of the decanter 8. By such washing with water, the small amount of methanol in the organic layer is dissolved in water and removed. Ther tertiary olefin discharged form the decanter 8 is delivered to an adsorption tower 9 or 9', wherein traces of water and the primary alcohol are removed by adsorption, to provide the product tertiary olefin. The aqueous layer form the decanter 8 is pre-heated in a pre-heater 10 and delivered to a distillation column 11. The vapor of the primary alcohol is discharged from the top of the distillation column 11 and condensed in condenser 12 to recover a liquid primary alcohol. Water is accumulated at the bottom of the distillation column 11. The water is discharged from the bottom of distillation column 11 and a part thereof is delivered through line 13 to a reboiler 14, wherein it is changed to steam, which steam is in turn recycled to the distillatiuon column 11. Also, a part of the water is discharged out of the system through line 15 or provided for use in washing in the decanter 8. The remainder of the water is delivered through line 16 and heated in a heat exchanger 5 for conversion into steam. The steam is delivered through line 17 to a superheater 18, wherein it is further heated to be converted to superheated steam. The superheated steam is mixed with the pre-heated gaseous tertiary ether through line 19 into line 12. If necessary, it is also possible to supplement steam from the branch pipe 20 of conduits 17.

According to the present invention, conversion of tertiary ether as well as selectivity of tertiary olefin and a primary alcohol are all very high. As a result the problems of purification can be greatly reduced. In fact, the purification operation may sometimes be eliminated. In addition, the catalyst life is markedly elongated. Thus, a process to produce high purity tertiary olefins with many commercial advantages has been provided. These advantages include easy catalyst preparation at low cost, good reproducibility and easy regeneration of the catalyst. Moreover, abrupt lowering of the reaction temperature during the reaction can be avoided and heat from the outside can be provided very easily.

Clearly, the present invention is very valuable industrially.

The invention will be illustrated in the following nonlimiting examples.

EXAMPLES 1-5 AND COMPARATIVE EXAMPLE 1

A drying agent, on the market Neobead D ($Al_2O_3$: 90 wt.%, $SiO_2$: 10 wt.%; manufactured by Mizusawa Industrial Chemicals, Ltd.) was ground to a particle size of 10-30 mesh and calcined under the conditions shown in Table 1. Then 20 cc of the product was charged in a reaction column made of stainless steel having an inside diameter of 16 mm$\phi$ and a length of 50 cm and the cracking reaction of MTBE was conducted. The calcination conditions, reaction conditions and the results obtained are shown in Table 1.

TABLE 1

| Number of Example | 1 | 2 | 3 | 4*1 | 5 | Comp. 1 |
|---|---|---|---|---|---|---|
| Catalyst*2 | | | | | | |
| Calcination temperature (°C.) | 800 | 1000 | 1000 | 1000 | 1000 | 600 |
| Calcination time (hrs) | 6 | 6 | 24 | 24 | 6 | 6 |
| Reaction conditions | | | | | | |
| Reaction pressure (kg/cm² gauge) | 5 | 5 | 5 | 5 | 2 | 5 |
| Preheating temperature (°C.) | 200 | 200 | 200 | 250 | 180 | 200 |
| Reaction temperature (°C.) | 200 | 200 | 200 | 250 | 180 | 200 |
| WHSV (g/cc/hr) | 2 | 2 | 2 | 4 | 2 | 2 |
| Results | | | | | | |
| Conversion of MTBE (%) | 96.8 | 96.7 | 95.2 | 98.1 | 85.2 | 76.5 |
| Selectivity of isobutylene (mol. %) | 99.9 | 100 | 100 | 99.8 | 100 | 98.7 |
| Selectivity of methanol (mol. %) | 96.4 | 97.5 | 98.5 | 98.3 | 99.5 | 93.5 |
| Selectivity of dimethyl ether (mol. %) | 3.6 | 2.5 | 1.5 | 1.7 | 0.5 | 6.5 |
| Selectivity of diisobutylene (mol. %) | Trace | — | — | 0.2 | 0.0 | 1.3 |

Notes:
*1 The reaction was continued for 100 hours; however, the results of reaction showed no substantial deterioration.
*2 The calcination was conducted by gas-passing form using a quartz tube in a cylindrical electric furnace.

EXAMPLES 6-10 AND COMPARATIVE EXAMPLES 2 AND 3

A silica-alumina catalyst N-631 L on the market ($Al_2O_3$: 13%, $SiO_2$: 87%; manufactured by NIKKI CHEMICAL CO., LTD.) was ground to a particle size of 10-30 mesh and calcined under the conditions shown in Table 2. Using each of these catalysts, the reaction was conducted according to the same procedure same as in Examples 1-5. The calcination conditions, reaction conditions and the results obtained are shown in Table 2.

TABLE 2

| Number of Example | 6 | 7 | 8 | 9*2 | 10 | Comp. 2 | Comp. 3 |
|---|---|---|---|---|---|---|---|
| Catalyst*1 | | | | | | | |
| Calcination temperature (°C.) | 1000 | 1000 | 1000 | Regenerated at 500° C. | 1000 | 600 | 600 |
| Calcination time (hrs) | 6 | 6 | 24 | | 24 | 6 | 6 |
| Reaction conditions | | | | | | | |
| Reaction pressure (kg/cm² gauge) | 5 | 5 | 5 | 5 | 10 | 5 | 5 |
| Preheating temperature (°C.) | 240 | 200 | 250 | 250 | 200 | 200 | 170 |
| Reaction temperature (°C.) | 240 | 200 | 250 | 250 | 280 | 200 | 170 |
| WHSV (g/cc/hr) | 3.0 | 3.0 | 2.5 | 2.5 | 8.0 | 3.0 | 2.0 |
| Results | | | | | | | |
| Conversion of MTBE (%) | 99.0 | 96.2 | 99.5 | 99.3 | 97.5 | 98.0*3 | 91.4* |
| Selectivity of isobutylene (mol. %) | 99.8 | 99.9 | 99.6 | 99.7 | 99.3 | 37.3 | 76.8 |
| Selectivity of methanol (mol. %) | 98.8 | 99.6 | 99.0 | 99.1 | 99.2 | 86.5 | 96.9 |
| Selectivity of dimethyl ether (mol. %) | 1.2 | 0.4 | 1.0 | 0.9 | 0.8 | 13.5 | 3.0 |
| Selectivity of diisobutylene (mol. %) | 0.2 | 0.1 | 0.4 | 0.3 | 0.7 | 36.5 | 15.8 |

Notes:
*1 The calcination was conducted according to gas-passing form by allowing air to pass through a quartz column having an inside diameter of 20 mm$\phi$ at a rate of 5 l/hr.
*2 Using the catalyst same as that in Example 8, the reaction was continued for 50 hours. Then the conversion of MTBE decreased to 97%. Accordingly, regeneration was carried out by allowing air having a temperature of 500° C. to pass at a rate of 2 l/hr for 2 hours and it was used for the reaction in Example 9 after confirmation of no generation of $CO_2$.
*3 The conversion decreased to 90% after 10 hours elapsed.
*4 The conversion decreased to 80% after 17 hours elapsed.

EXAMPLES 11-13 AND COMPARATIVE EXAMPLES 4-7

A water glass solution ($SiO_2$: 4.7%) and carbon dioxide were allowed to react to obtain a slurry of silica hydrogel. After aging, a predetermined amount of aqueous alumina solution ($Al_2O_3$: 7.3%) was added to deposit alumina on silica hydrogel. After further aging, ammonia water was added to adjust the pH to 8.0. The product was filtered, washed to remove ammonia and ground to a particle size of 10–30 mesh and calcined at 600° C. in a quartz column for 24 hours while allowing the passage of air. Thus there were obtained silica-alumina compound A and silica-alumina compound B, respectively. The composition of both compounds were as follows:

|  | $Al_2O_3$ | $SiO_2$ |
|---|---|---|
| Silica-alumina compound A | 25% | 75% |
| Silica-alumina compound B | 2% | 98% |

These silica-alumina compounds were further calcined and used for the cracking reaction according to the same procedure as that in Examples 1–5. The calcination conditions, reaction conditions and the results are shown in Table 3.

TABLE 3

|  | Silica-alumina compound A | | | Silica-alumina compound B | | | |
|---|---|---|---|---|---|---|---|
| Number of example | 11 | Comp. 4 | Comp. 5 | 12 | 13 | Comp. 6 | Comp. 7 |
| Catalyst*[1] | | | | | | | |
| Calcination temperature (°C.) | 800 | 1200 | 600 | 800 | 700 | 600 | 1200 |
| Calcination time (hrs) | 6 | 6 | 24 | 1 | 6 | 24 | 24 |
| Reaction conditions | | | | | | | |
| Reaction pressure ($kg/cm^2$ gauge) | 5 | 5 | 5 | 5 | 5 | 5 | 5 |
| Reaction temperature (°C.) | 200 | 250 | 200 | 200 | 200 | 200 | 250 |
| WHSV (g/cc/hr) | 2 | 2 | 2 | 2 | 2 | 2 | 2 |
| Results of reactions | | | | | | | |
| Conversion of MTBE (%) | 97.2 | 21.2 | 98.1 | 97.0 | 97.5 | 96.3 | no reaction occurred |
| Selectivity of isobutylene (mol. %) | 99.4 | 100 | 44.2 | 96.1 | 95.7 | 56.0 | no reaction occurred |
| Selectivity of methanol (mol. %) | 98.7 | 91 | 89.1 | 99.0 | 98.4 | 89.6 | no reaction occurred |
| Selectivity of dimethyl ether (mol. %) | 1.3 | 9 | 10.9 | 1.0 | 1.6 | 10.4 | no reaction occurred |
| Selectivity of di-isobutylene (mol. %) | 0.6 | 0 | 30.5 | 3.9 | 4.3 | 20.4 | no reaction ocurred |

Note:
*[1]Calcination was conducted in a stationary form using a muffle furnace.

EXAMPLE 14

Using the catalyst obtained according to the procedure same as that in Example 8, the cracking of methyl-tert-amyl ether was conducted. Reaction conditions and results are shown in Table 4.

TABLE 4

| Reaction conditions | |
|---|---|
| Reaction pressure ($kg/cm^2$ gauge) | 5 |
| Preheating temperatures (°C.) | 200 |
| Reaction temperature (°C.) | 200 |
| WHSV (g/cc/hr) | 3 |
| Results | |
| Conversion of methyl-tert-amyl ether (%) | 98.9 |
| Selectivity of tertiary olefin (mol. %) | 99.2 |
| Selectivity of methanol (mol. %) | 99.1 |
| Selectivity of dimethyl ether (mol. %) | 0.9 |

TABLE 4-continued

| Selectivity of olefindimer (mol. %) | 0.8 |
|---|---|

EXAMPLE 15

Using the catalyst obtained according to the procedure of Example 7, the cracking of ethyl-tert-butyl ether was conducted. Reaction conditions and results are shown in Table 5.

TABLE 5

| Reaction conditions | |
|---|---|
| Reaction pressure ($kg/cm^2$ gauge) | 5 |
| Preheating temperature (°C.) | 250 |
| Reaction temperature (°C.) | 250 |
| WHSV (g/cc/hr) | 4 |
| Results | |
| Conversion of ethyl-tert-butyl ether (%) | 99.3 |
| Selectivity of isobutylene (mol. %) | 99.7 |
| Selectivity of ethanol (mol. %) | 99.2 |
| Selectivity of diethyl ether (mol. %) | 0.8 |
| Selectivity of diisobutylene (mol. %) | 0.3 |

EXAMPLES 16–19

A silica-alumina catalyst N-631 L ($Al_2O_3$: 13%. $SiO_2$: 87%; manufactured by NIKKI CHEMICAL CO., LTD.) was ground to a particle size of 10–30 mesh and calcined. Then 13 cc of the catalyst was charged in a reaction column made of stainless steel having an inside diameter of 12 mm$\phi$ and a length of 30 cm and the cracking reaction of MTBE was conducted. The calcination conditions, reaction conditions and the results obtained are shown in Table 6.

COMPARATIVE EXAMPLE 8

Example 17 was repeated except that the calcination condition for preparation of the catalyst was changed.

The calcination condition and the result are shown in Table 6.

COMPARATIVE EXAMPLE 9

Example 17 was repeated except that no steam was present in the reaction system.

The result is shown in Table 6.

TABLE 6

| Number of example | 16 | 17 | 18 | 19 | Comp. 8 | Comp. 9 |
|---|---|---|---|---|---|---|
| Catalyst | | | | | | |
| Calcination temperature (°C.) | 800 | 1000 | 1000 | 1000 | 600 | 1000 |
| Calcination time (hrs) | 6 | 24 | 24 | 6 | 6 | 24 |
| Reaction conditions | | | | | | |
| Reaction pressure (kg/cm² gauge) | 5 | 5 | 5 | 5 | 5 | 5 |
| Reaction temperature (°C.) | 250 | 250 | 300 | 300 | 250 | 250 |
| Steam ratio (molar ratio) | 3.0 | 5.0 | 5.0 | 18.0 | 5.0 | no addition |
| MTBE WHSV (g/cc/hr) | 2.5 | 2.5 | 3.0 | 2.0 | 2.5 | 2.5 |
| Results | | | | | | |
| Sampling time (hrs)* | 5 | 5 | 50 | 100 | 5 | 5 |
| Conversion of MTBE (%) | 99.7 | 99.2 | 99.9 | 99.3 | 99.8 | 99.5 |
| Selectivity of isobutylene (mol. %) | 99.2 | 99.8 | 99.8 | 99.9 | 94.2 | 99.6 |
| Selectivity of methanol (mol. %) | 99.9 | 100 | 100 | 100 | 98.6 | 99.0 |
| Selectivity of dimethyl ether (mol. %) | 0.1 | 0 | 0 | 0 | 1.3 | 1.0 |
| Selectivity of diisobutylene (mol. %) (+triisobutylene) | 0.3 | 0.1 | 0.1 | 0 | 5.2 | 0.4 |
| Selectivity of t-butanol (mol. %) | 0.2 | 0.1 | 0.1 | 0.1 | 0.6 | — |

Note:
*Lapse from the time when the reaction has reached steady state to the time of sampling.

EXAMPLES 20–23

A drying agent, Neobead D ($Al_2O_3$: 90 wt.%, $SiO_2$: 10 wt.%; manufactured by Mizusawa Industrial Chemicals, Ltd.) was ground to a particle size of 10–30 mesh and calcined. Then 13 cc of the catalyst was charged in a reaction column made of stainless steel having an inside diameter of 12 mmφ and a length of 30 cm and cracking reactions of various tertiary ethers were conducted. The tertiary ethers employed, calcination conditions, reaction conditions and the results obtained are shown in Table 7.

COMPARATIVE EXAMPLE 10

Example 20 was repeated except that the calcination condition for preparation of the catalyst was changed. The calcination condition and the result are shown in Table 7.

COMPARATIVE EXAMPLE 11

Example 20 was repeated except that no steam was present in the reaction system.

The result is shown in Table 7.

COMPARATIVE EXAMPLE 12

Example 20 was repeated except that the calcination condition for preparation of the catalyst was changed. The calcination condition and the result are shown in Table 7.

TABLE 7

| Number of example | 20 | 21 | 22 | 23 | Comp. 10 | Comp. 11 | Comp. 12 |
|---|---|---|---|---|---|---|---|
| Tertiary ether employed | MTBE | MTBE | methyl-t-amyl-ether | ethyl-t-butyl-ether | MTBE | MTBE | MTBE |
| Catalyst | | | | | | | |
| Calcination temperature (°C.) | 1000 | 1000 | 1000 | 1000 | 1200 | 1000 | 600 |
| Calcination time (hrs) | 6 | 6 | 6 | | 6 | 6 | 6 |
| Reaction conditions | | | | | | | |
| Reaction pressure (kg/cm² gauge) | 5 | 5 | 5 | 5 | 5 | 5 | 5 |
| Reaction temperature (°C.) | 300 | 300 | 300 | 250 | 300 | 300 | 300 |
| Steam ratio (molar ratio) | 5.0 | 5.0 | 5.0 | 5.0 | 5.0 | no addition | 5.0 |
| WHSV of tertiary ether (g/cc/hr) | 2.0 | 2.0 | 2.0 | 2.0 | 2.0 | 2.0 | 2.0 |
| Results | | | | | | | |
| Sampling time* (hrs.) | 5 | 300 | 100 | 100 | 5 | 5 | 5 |
| Conversion of tertiary ether (%) | 99.7 | 99.8 | 99.9 | 99.2 | no reaction | 99.1 | 99.9 |
| Selectivity of tertiary olefin (mol. %) | 99.8 | 99.9 | 99.5 | 99.7 | no reaction | 99.6 | 99.4 |
| Selectivity of alcohol (mol. %) | 99.6 | 99.7 | 99.7 | 99.5 | no reaction | 97.2 | 92.4 |
| Selectivity of dialkyl ether (mol. %) | 0.4 | 0.3 | 0.3 | 0.5 | no reaction | 2.8 | 7.6 |
| Selectivity of olefin dimer (mol. %) | 0.2 | 0.1 | 0.4 | 0.3 | no reaction | 0.3 | 0.5 |
| Selectivity of | 0 | 0 | 0.1 | 0 | no | 0.1 | 0.1 |

TABLE 7-continued

| Number of example | 20 | 21 | 22 | 23 | Comp. 10 | Comp. 11 | Comp. 12 |
|---|---|---|---|---|---|---|---|
| tertiary alcohol (mol. %) | | | | | reaction | | |

Note:
*Lapse from the time when the reaction has reached steady state to the time of sampling.

EXAMPLE 24

The catalyst activity with lapse of time when steam is present in the reaction system is shown by the straight line (a) in FIG. 2.

| Catalyst: | Silica-alumina, N-631 L, calcined at 1000° C. for 24 hours. |
|---|---|
| Tertiary ether employed: | MTBE |
| Reaction temperature: | 250° C. |
| Reaction pressure: | 5 kg/cm² (gauge) |
| Steam ratio (molar ratio): | 5.0 |
| WHSV of MTBE: | 2.0 g/cc/hr |

EXAMPLE 25

The catalyst activity with lapse of time when Example 24 was repeated except that no steam was present in the reaction system is shown by the curve (b) in FIG. 2.

What is claimed is:

1. A process for producing the corresponding tertiary olefin from a tertiary ether which comprises contacting in the presence of steam a gaseous tertiary ether with a catalyst obtained by calcining a silica-alumina compound at 700°–1100° C., the molar ratio of steam to tertiary ether being from 0.3 to 50.

2. The process as claimed in claim 1 wherein the weight percent of silica and alumina based on the total weight of silica and alumina are 2–98 wt.% and 98–2 wt.%, respectively.

3. The process as claimed in claim 1 wherein the calcination temperature of silica-alumina compound is 750°–1000° C.

4. The process as claimed in claim 1 wherein the calcination time of silica-alumina compound is 0.5–50 hours.

5. The process as claimed in claim 1 wherein tertiary ethers represented by the following general formula:

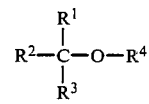

wherein $R^1$, $R^2$ and $R^3$ are alkyl groups each having 1–4 carbon atoms which may be the same or different and $R^4$ is an alkyl group having 1–3 carbon atoms are used as the raw material.

6. The process as claimed in claim 5 wherein a compound selected from the group consisting of methyl-tert-butyl ether, ethyl-tert-butyl ether, methyl-tert-amyl ether, 2,3-dimethyl-2-methoxybutane, 2-methoxy-2-methyl-pentane and 3-methoxy-3-methylpentane is used as the raw material.

7. The process as claimed in claim 1 wherein the reaction temperature at which a tertiary olefin is produced from the corresponding tertiary ether is 120°–350° C.

8. The process as claimed in claim 7 wherein the reaction temperature is 170°–300° C.

9. The process as claimed in claim 1 wherein the velocity at which tertiary ether is supplied per unit volume of catalyst (WHSV) is 0.3–100 g/cc/hr.

10. The process as claimed in claim 1 wherein the velocity at which tertiary ether is supplied per unit of volume of catalyst (WHSV) is 0.5–10 g/cc/hr.

11. The process as claimed in claim 1 wherein the velocity at which tertiary ether is supplied per unit volume of catalyst (WHSV) is 0.5–30 g/cc/hr.

12. The process as claimed in claim 1 wherein the molar ratio of steam to tertiary ether is from 0.5 to 30.

13. The process as claimed in claim 1 wherein the reaction temperature at which a tertiary olefin is produced from the corresponding tertiary ether is 150°–400° C.

14. The process as claimed in claim 1 wherein the reaction temperature at which a tertiary olefin is produced from the corresponding tertiary ether is 180°–350° C.

* * * * *